United States Patent [19]

Fujisawa et al.

[11] Patent Number: 5,757,955
[45] Date of Patent: May 26, 1998

[54] METHOD FOR CHECKING A CONNECTION OF WIRES AND CONTROL APPARATUS

[75] Inventors: Atsushi Fujisawa; Akihiro Komori; Shigeki Furukawa. all of Yokkaichi. Japan

[73] Assignee: Sumitomo Wiring Systems, Ltd.. Japan

[21] Appl. No.: 576,960

[22] Filed: Dec. 22, 1995

[30] Foreign Application Priority Data

Jan. 5, 1995 [JP] Japan ................... 7-000266

[51] Int. Cl.$^6$ ........................................... G06T 7/60
[52] U.S. Cl. ...................... 382/141; 382/150; 382/164
[58] Field of Search ........................... 382/152, 150, 382/149, 141, 162, 164, 165, 173, 194, 206, 286; 356/379, 237, 425; 439/730, 880, 877, 912, 932; 348/86, 90, 93, 125, 126; 364/468.17, 564; 228/9; 250/559.34, 559.46

[56] References Cited

U.S. PATENT DOCUMENTS

| | | | |
|---|---|---|---|
| 4,271,330 | 6/1981 | Watine et al. | 174/84 R |
| 4,283,596 | 8/1981 | Vidakovits et al. | 174/84 R |
| 4,547,897 | 10/1985 | Peterson | 382/162 |
| 4,832,248 | 5/1989 | Soni et al. | 228/56.3 |
| 5,157,463 | 10/1992 | Brown et al. | 356/394 |
| 5,483,603 | 1/1996 | Luke et al. | 382/147 |
| 5,562,243 | 10/1996 | Marcantonio | 228/8 |

FOREIGN PATENT DOCUMENTS

90/07202  6/1990  WIPO .

OTHER PUBLICATIONS

Shigeki Kobayashi et al.. *Identifying Solder Surface Orientation from Color Highlight Images*. Omron Institute of Life Science. Apr. 1990. pp. 821–825.

*Primary Examiner*—Leo Boudreau
*Assistant Examiner*—Brian P. Werner
*Attorney, Agent, or Firm*—Anthony J. Casella; Gerald E. Hespos; Ludomir A. Budzyn

[57] ABSTRACT

A color image pickup 33 picks up a color image of cores 9 soldered to the inner wall of a metal tube 12 of a connector 11 by a solder 16b. A component image of the color of the cores 9 is extracted from the color image. A non-soldered area of the cores 9 exposed from the solder 16b is calculated based on the extracted component image. The calculated non-soldered area is compared with a first threshold value to determine whether or not the cores 9 are satisfactorily soldered (i.e., the wires are satisfactorily connected). Connection of the wires can be checked with a uniform quality and an improved accuracy.

14 Claims, 4 Drawing Sheets

METHOD FOR CHECKING A CONNECTION OF WIRES AND CONTROL APPARATUS

BACKGROUND OF THE INVENTION

1. Field of the Invention

The present invention relates to a method for checking a connection of wires, in particular to a method for checking a connection of wires connected via a connector and to a control apparatus for a connector heating apparatus, in particular for the implementation of the above method.

2. Description of the Prior Art

Wires are connected, for example, via a connector 11 as shown in a sectional top view of FIG. 3(a) and a sectional side view of FIG. 3(b). In this connector 11, the outer wall of a metal tube 12 formed of brass and plated with tin is cut in a keyhole shape in two intermediate positions, the outer longitudinal ends of the keyhole-shaped cuts still being integral with the outer wall of the metal tube 12. The keyhole-shaped cuts are bent inward by pressing the inner longitudinal ends of the keyhole-shaped cuts inward to form a pair of flaps 13 and a pair of check holes 14. Further, a solder mount hole 17 is formed in a longitudinal middle portion of the outer surface of the metal tube 12. A disk-shaped solder 16a is mounted in the metal tube 12 through the hole 17. Tubular hot melts 19a of polypropylene project from the opposite longitudinal ends of the metal tube 12. The hot melts 19a are blue before heating, and soften and become transparent after heating. A semitransparent heat shrinkable tube 21a of polyolefin covers the metal tube 19 and the hot melts 19a. Upon being subjected to heat, the heat shrinkable tube 21a shrinks, thereby clinching the metal tube 12 and the hot melts 19a to seal the metal tube 12.

Hereafter, a method for connecting wires 10 via the above connector 11 is described. As shown in FIG. 4, the wires 10 each having an exposed core 9 of copper are inserted into the metal tube 12 through the interior of the corresponding hot melts 19a. At this stage, the cores 9 are pressed by the flaps 13 to be brought into close contact with the inner wall of the metal tube 12 in positions facing the check holes 14. The connector 11 into which the wires 10 are inserted in this way is heated by an unillustrated heating means such as a heater. Then, as shown in FIG. 5, the solder 16a provided in the metal tube 12 melts, thereby adhering the cores 9 to the inner wall of the metal tube 12, and softened hot melts 19b are clinched by the heat shrinkable tube 21b, thereby sealing the opposite longitudinal ends of the connector 11 to securely hold the wires 10.

In checking the connection of the wires 10 via the above connector 11, i.e. in detecting after heating whether the cores 9 of the wires 10 are satisfactorily adhered to the inner wall of the metal tube 12 by a molten solder 16b, whether the hot melts 19b were satisfactorily softened, and whether the heat shrinkable tube 21b satisfactorily shrunk, if a detection is visually made, a satisfactory level of the connection of the wires may differ depending upon who makes a detection because of different detection criteria. Further, a checker may overlook a defective connection due to fatigue or other reason.

In view of the above problem, an object of the invention is to provide an improved method for checking a connection of wires and an improved control apparatus for a connector heating apparatus, in particular for the implementation of the method according to the invention, which assure a checking of a uniform quality and with which a checking can be performed in particular without overlooking a defective connection.

SUMMARY OF THE INVENTION

According to the invention, there is provided a method for checking a connection of electric wires, in particular connected via a connector, comprising:

an image pickup step of picking up a color image of a connection region including at least part of an area of connection of the electric wires by means of color image pickup means, an image extraction step of extracting a predetermined or predeterminable image color component from the color image, a defect area calculation step of calculating an area of defect from the extracted image color component, and a determination step of determining whether the connection is satisfactory.

According to a preferred embodiment, the determining in the determination step is performed based on the defect area determined in the defect area calculation step.

Preferably, the image pickup step comprises a first image pickup step of picking up a color image of a first region of the connection region, the first region including at least part of an area of soldering of the electric wires, preferably with the connector.

Further preferably, the image extraction step comprises a first image extraction step of extracting a predetermined or predeterminable first image color component of a color of the wires from the color image picked up by the color image pick up means.

Further preferably, the defect area calculation step comprises a non-soldered area calculation step of calculating a non-soldered area of the defect area, in particular based on the color of the cores of the wires, wherein the determination step comprises preferably a first determination step of determining that the cores of the wires are satisfactorily soldered, in particular to the connector, when the calculated non-soldered area is smaller than a first threshold value, while determining that the cores of the wires are not satisfactorily soldered, in particular to the connector, when the calculated non-soldered area is larger than or equal to the first threshold value.

According to a further embodiment of the present invention, the image pickup step comprises a second image pickup step of picking up a color image of a second region of the connection region, the second region including at least part of an area of hot melt means of the connector by means of color image pickup means.

Preferably, the image extraction step comprises a second image extraction step of extracting a predetermined or predeterminable second image color component of a color of hot melt means of the connector before heating from the color image picked up by the color image pickup means, wherein the defect area calculation step comprises preferably a non-softened area calculation step of calculating a non-softened area of the hot melt means of the defect area from the extracted second image color component of the color of the hot melt means.

Further preferably, the determination step comprises a second determination step of determining that the hot melt means was satisfactorily softened when the calculated non-softened area is smaller than a second threshold value while determining that the hot melt means was not satisfactorily softened when the calculated non-softened area is larger than or equal to the second threshold value.

According to still a further embodiment, the image pickup step comprises a third image pickup step of picking up a color image of a predetermined third region of the connection region by means of the color image pickup means.

Preferably, the image extraction step comprises a third image extraction step of extracting a black image component from the color image picked up by the color image pick up means, wherein the defect area calculation step comprises preferably a carbonized area calculation step of calculating a carbonized area of the connection from the extracted black image component.

Further preferably, the determination step comprises a third determination step of determining that the connection is not carbonized when the calculated carbonized area is smaller than a third threshold value while determining that the connection is carbonized and thus unsatisfactory, when the calculated carbonized area is larger than or equal to the third threshold value.

According to a further embodiment, the method further comprises an automatic heating control step of automatically decreasing a heating temperature of a heating means or shortening a heating time of the heating means when the connection is determined to be carbonized in the third determination step.

Further preferably, the method further comprises an additional automatic heating control step of automatically increasing a heating temperature of a heating means or prolonging a heating time of the heating means when the connection is determined to be unsatisfactory in the determination step or when the softening of the hot melt means is determined to be unsatisfactory in the second determination step.

According to the invention, there is further provided a control apparatus for a connection heating apparatus, in particular for the implementation of a method according to one of the preceding paragraphs, wherein the control apparatus comprises:

a color image pickup means for picking up a color image of an object, in particular a connection, an image extracting means for extracting a predetermined or predeterminable image color component from the color image, an image processing means for processing the image color component in order to calculate a defect area of the object, and a discriminator means for discriminating whether the object is satisfactory and for outputting a control signal.

According to a preferred embodiment, the control apparatus further comprises a control means for receiving the control signal outputted from the discriminator means for controlling an external apparatus, in particular a connection heating apparatus, based on the control signal.

According to a preferred embodiment, there is provided a method for checking a connection of insulated wires connected via a connector comprising in particular a metal tube, a pair of flaps and a pair of check holes formed by cutting the outer wall of the metal tube in two positions such that the outer longitudinal ends of the cuts are still integral with the outer wall of the metal and pressing the inner longitudinal ends of the cuts inward to bend the cut portions inward, a pair of tubular hot melts which extend from the opposite longitudinal ends of the metal tube and change their color and soften upon being subjected to heat, a heat shrinkable tube which covers the metal tube and the hot melts and shrinks upon being subjected to heat, and a solder provided in a center portion of the metal tube, the connector being heated by heating means after the wires are inserted into the metal tube through the interior of the hot melts from the opposite longitudinal ends of the connector and cores of the wires exposed from insulating sheaths of the wires are pressed against the inner wall of the metal tube by the flaps in positions facing the check holes, whereby the solder is molten to adhere the cores of the wires at their ends to the inner wall of the metal tube and the heat shrinkable tube clinches the softened hot melts, thereby sealing the opposite longitudinal ends of the connector, comprising:

a first color image pickup step of picking up an image of a first region including an area where the cores are soldered to the inner wall of the metal tube through the check holes by means of color image pickup means, a first image extraction step of extracting a component image of the color of the cores from the color image picked up by the color image pick up means, a non-soldered area calculation step of calculating a nonsoldered area of the cores from the extracted component image of the color of the cores, and a first determination step of determining that the cores are satisfactorily soldered to the inner wall of the metal tube when the calculated non-soldered area is smaller than a first threshold value while determining that the cores are not satisfactorily soldered to the inner wall of the metal tube when the calculated non-soldered area is larger than the first threshold value.

Accordingly, the checking method comprises the first color image pickup step of picking up the image of the first region including the area where the cores are soldered to the inner wall of the metal tube through the check holes by means of the color image pickup means, the first image extraction step of extracting the component image of the color of the cores from the color image picked up by the color image pick up means, the non-soldered area calculation step of calculating the non-soldered area of the cores from the extracted component image of the color of the cores, and the first determination step of determining that the cores are satisfactorily soldered to the inner wall of the metal tube when the calculated non-soldered area is smaller than the first threshold value while determining that the cores are not satisfactorily soldered to the inner wall of the metal tube when the calculated non-soldered area is larger than the first threshold value. Accordingly, if the molten solder does not entirely cover the exposed cores, i.e. the cores are exposed from the molten solder, the non-soldered area is calculated based on the component image of the color of the exposed cores and compared with the first threshold value. In this way, whether or not the cores are satisfactorily soldered can be mechanically checked.

As described above, whether or not the cores are satisfactorily soldered can be mechanically checked. Therefore, the soldering of the wires to the inner wall of the metal tube (connection of the wires) can be checked with a uniform quality and a defective soldering can be detected with an enhanced accuracy.

Further, there may be provided a first automatic heating control step of automatically increasing a heating temperature of the heating means or prolonging a heating time of the heating means when the soldering by the solder is determined to be unsatisfactory in the first determination step of the above checking method.

Accordingly, heating may be automatically so controlled as to increase the heating temperature of the heating means or to prolong the heating time of the heating means if the cores are determined to be unsatisfactorily soldered in the first determination step, i.e. in the case of insufficient heating. This effectively prevents the cores from being unsatisfactorily soldered.

If the heating temperature or heating time of the heating means is controlled in such a manner, the defective soldering of the cores can be effectively prevented.

According to a further preferred embodiment there is provided a method for checking a connection of insulated wires connected in particular via a connector comprising a metal tube, a pair of flaps and a pair of check holes formed by cutting the outer wall of the metal tube in two positions such that the outer longitudinal ends of the cuts are still integral with the outer wall of the metal and pressing the inner longitudinal ends of the cuts inward to bend the cut portions inward, a pair of tubular hot melts which extend from the opposite longitudinal ends of the metal tube and change their color and soften upon being subjected to heat, a heat shrinkable tube which covers the metal tube and the hot melts and shrinks upon being subjected to heat, and a solder provided in a center portion of the metal tube, the connector being heated by heating means after the wires are inserted into the metal tube through the interior of the hot melts from the opposite longitudinal ends of the connector and cores of the wires exposed from insulating sheaths of the wires pressed against the inner wall of the metal tube by the flaps in positions facing the check holes, whereby the solder is molten to adhere the cores of the wires at their ends to the inner wall of the metal tube and the heat shrinkable tube clinches the softened hot melts, thereby sealing the opposite longitudinal ends of the connector, comprising:

a second color image pickup step of picking up an image of a second region including the hot melts by means of color image pickup means, a second image extraction step of extracting a component image of the color of the hot melts before heating from the color image picked up by the color image pickup means, a non-softened area calculation step of calculating a nonsoftened area of the hot melts from the extracted component image of the color of the hot melts, and a second determination step of determining that the hot melts were satisfactorily softened when the calculated non-softened area is smaller than a second threshold value while determining that the hot melts were not satisfactorily softened when the calculated non-softened area is larger than the second threshold value.

The above checking method comprises the second color image pickup step of picking up the image of the second region including the hot melts by means of the color image pickup means, the second image extraction step of extracting the component image of the color of the hot melts before heating from the color image picked up by the color image pickup means, the non-softened area calculation step of calculating the non-softened area of the hot melts from the extracted component image of the color of the hot melts, and the second determination step of determining that the hot melts were satisfactorily softened when the calculated non-softened area is smaller than a second threshold value while determining that the hot melts were not satisfactorily softened when the calculated non-softened area is larger than the second threshold value. Accordingly, the insufficiently softened hot melts are extracted as the component image of the color of the hot melts before heating and compared with the second threshold value. In this way, whether or not the hot melts were satisfactorily softened can be mechanically checked.

Further, whether or not the hot melts were satisfactorily softened can be mechanically checked. Therefore, the softening of the hot melts (connection of the wires) can be checked with a uniform quality and a defective softening can be detected with an enhanced accuracy.

Further, there may be provided a second automatic heating control step of automatically increasing a heating temperature of the heating means or prolonging a heating time of the heating means when the softening of the hot melts is determined to be unsatisfactory in the second determination step of the above checking method.

Accordingly, heating may be automatically so controlled as to increase the heating temperature of the heating means or to prolong the heating time of the heating means if the hot melts are determined to have been unsatisfactorily softened in the second determination step, i.e. in the case of insufficient heating. This effectively prevents the hot melts from being unsatisfactorily softened.

If the heating temperature or heating time of the heating means is controlled such, the defective softening of the hot melts can be effectively prevented.

According to a further preferred embodiment of the invention, there is provided a method for checking a connection of insulated wires connected in particular via a connector comprising a metal tube, a pair of flaps and a pair of check holes formed by cutting the outer wall of the metal tube in two positions such that the outer longitudinal ends of the cuts are still integral with the outer wall of the metal and pressing the inner longitudinal ends of the cuts inward to bend the cut portions inward, a pair of tubular hot melts which extend from the opposite longitudinal ends of the metal tube and change their color and soften upon being subjected to heat, a heat shrinkable tube which covers the metal tube and the hot melts and shrinks upon being subjected to heat, and a solder provided in a center portion of the metal tube, the connector being heated by heating means after the wires are inserted into the metal tube through the interior of the hot melts from the opposite longitudinal ends of the connector and cores of the wires exposed from insulating sheaths of the wires pressed against the inner wall of the metal tube by the flaps in positions facing the check holes, whereby the solder is molten to adhere the cores of the wires at their ends to the inner wall of the metal tube and the heat shrinkable tube clinches the softened hot melts, thereby sealing the opposite longitudinal ends of the connector, comprising:

a third color image pickup step of picking up an image of a predetermined third region of the connector by means of color image pickup means, a third image extraction step of extracting a black component image from the color image picked up by the color image pick up means, a carbonized area calculation step of calculating a carbonized area of the connector from the extracted black component image, and a third determination step of determining that the connector is not carbonized when the calculated carbonized area is smaller than a third threshold value while determining that the connector is carbonized when the calculated carbonized area is larger than the third threshold value.

The above checking method comprises the third color image pickup step of picking up the image of the predetermined third region of the connector by means of the color image pickup means, the third image extraction step of extracting the black component image from the color image picked up by the color image pick up means, the carbonized area calculation step of calculating the carbonized area of the connector from the extracted black component image, and the third determination step of determining that the connector is not carbonized when the calculated carbonized area is smaller than the third threshold value while determining that the connector is carbonized when the calculated carbonized area is larger than the third threshold value. Accordingly, if the connector is carbonized due to excessive heating, the carbonized area is extracted as the black component image. The carbonized area is calculated based on the black component image and compared with the third threshold value. In this way, whether or not the connector is carbonized can be mechanically checked.

Accordingly, whether or not the connector is carbonized (connection of the wires) can be mechanically checked. Therefore, the carbonization of the connector can be checked with a uniform quality and detected with an enhanced accuracy.

Further, there may be provided a third automatic heating control step of automatically decreasing a heating temperature of the heating means or shortening a heating time of the heating means when the connector is determined to be carbonized in the third determination step of the above checking method.

Accordingly, heating may be automatically so controlled as to decrease the heating temperature of the heating means or to shorten the heating time of the heating means if the connector is determined to be carbonized in the third determination step, i.e. in the case of excessive heating. This effectively prevents the connector from being carbonized.

If the heating temperature or heating time of the heating means is controlled such, the carbonization of the connector can be effectively prevented.

BRIEF DESCRIPTION OF THE DRAWINGS

These and other objects, features and advantages of the present invention will become more apparent upon a reading of the following detailed description and accompanying drawings in which.

DETAILED DESCRIPTION OF THE PREFERRED EMBODIMENT

Figure 3A:
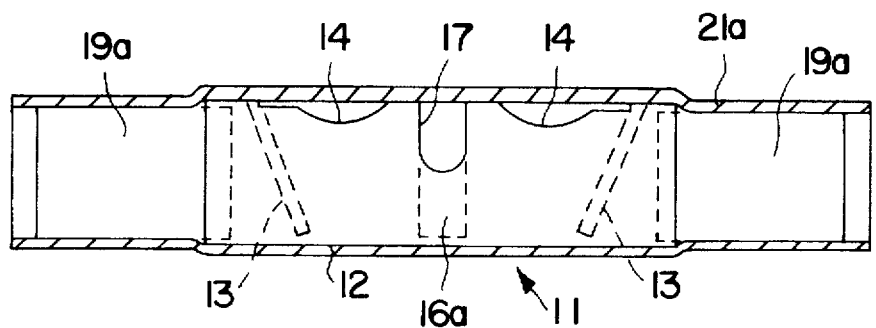
FIGS. 3(a) and 3(b) are sections of a prior art connector.
Figure 3B:
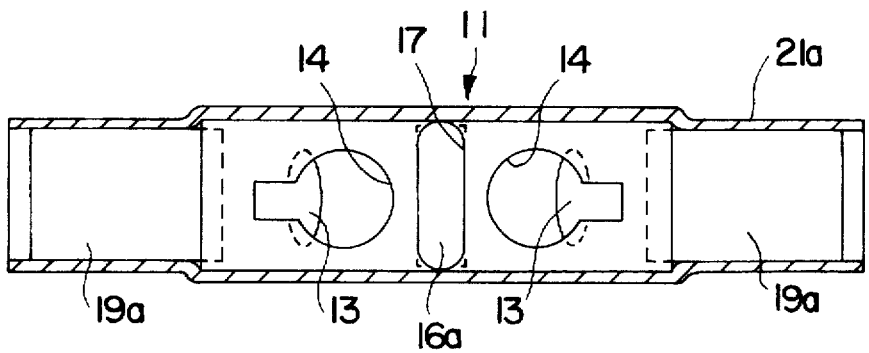
Figure 4:
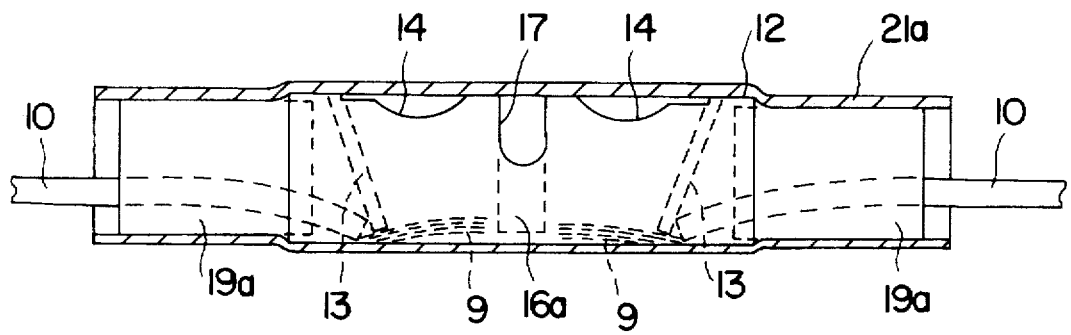
FIG. 4 is a section showing a state before the prior art connector is connected with wires.
Figure 5:
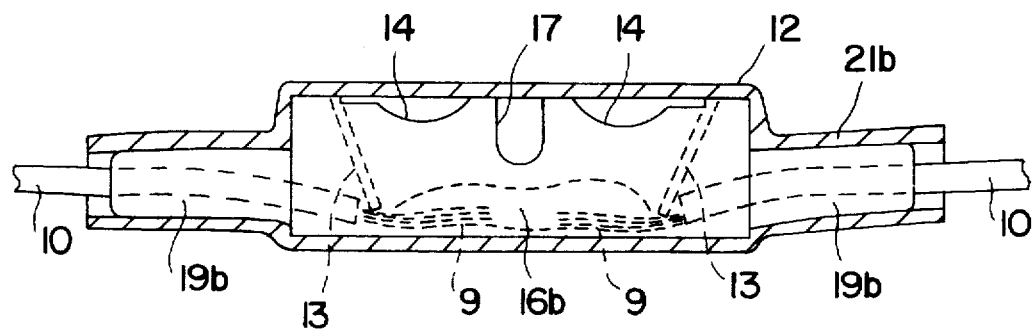
FIG. 5 is a section showing a state after the prior art connector is connected with the wires.

Hereafter, one embodiment of the invention is described with reference to the accompanying drawings. Since a connector and a wire connecting method by means of the connector according to this embodiment are same as those described with reference to the prior art shown in FIGS. 3 to 5, like or corresponding parts are identified by the same reference numerals and no description is given thereto.

Figure 1:
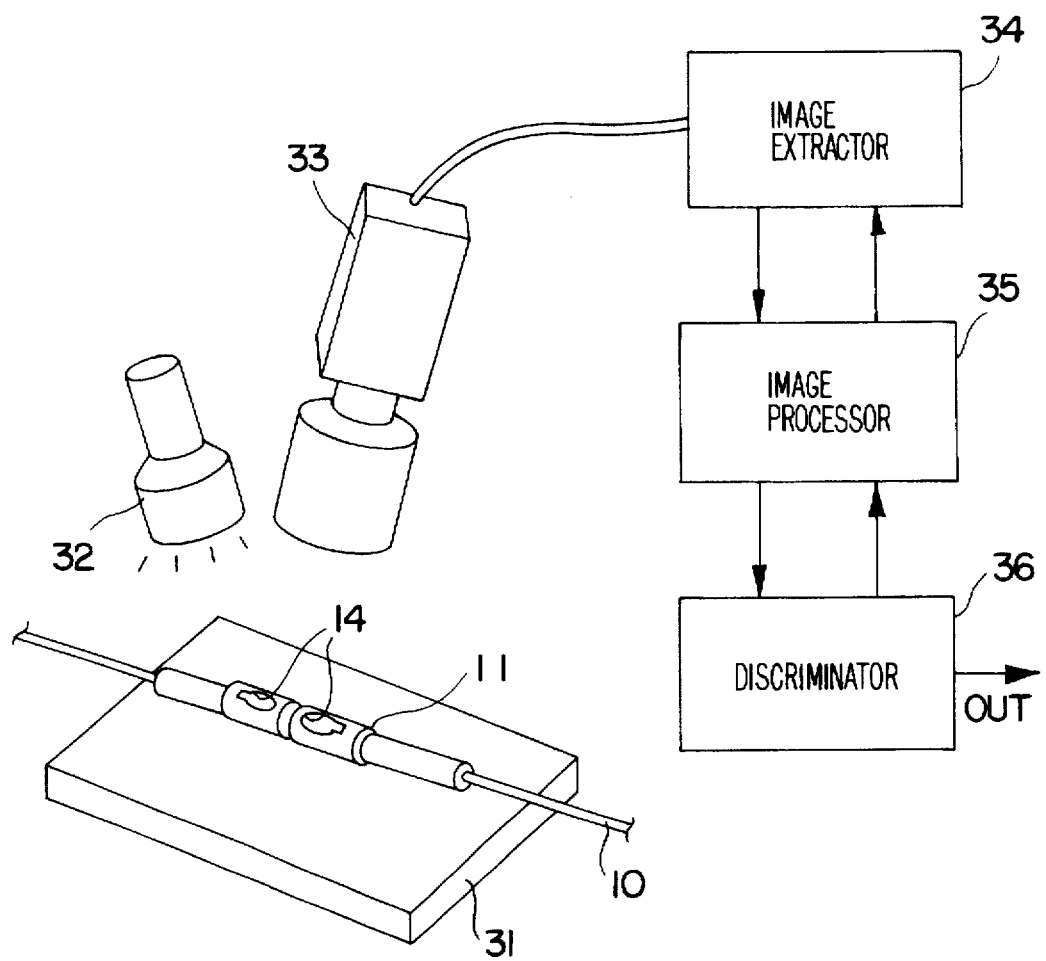
FIG. 1 is a diagram of one embodiment according to the invention.

FIG. 1 shows a connection checking apparatus used in association with a wire connection checking method as one embodiment of the invention. Specifically, the checking apparatus includes a plate-like checking table 31 on which a connector 11 connected with wires 10 is placed, an illuminating device 32 for projecting light upon the connector 11 placed on the checking table 31, a color image pickup 33 for picking up a color image of the connector 11 on the checking table 31, an image extracting device 34, an image processor 35 and a discriminator 36. The image extracting device 34 is electrically connected with the color image pickup 33 and is adapted to extract e.g. by means of filtering and/or masking a component image of a desired color from the color image picked up by the pickup 33. The image processor 34 calculates an area of the desired color based on the extracted component image. The discriminator 36 compares the area calculated by the image processor 35 with a predetermined threshold value and determines whether or not the connection of the wires 10 is satisfactory.

The checking method adopted by the above checking apparatus is described below. The connector 11 connected with the wires 10 is placed on the checking table 31 such that the check holes 14 of a metal tube 12 of the connector 11 face upward, i.e. face the color image pickup 33. In other words, the connector 11 is placed such that the color image pickup 33 can pick up an image of a molten solder 16b or cores 9 exposed from or not covered by the molten solder 16b.

Figure 2:
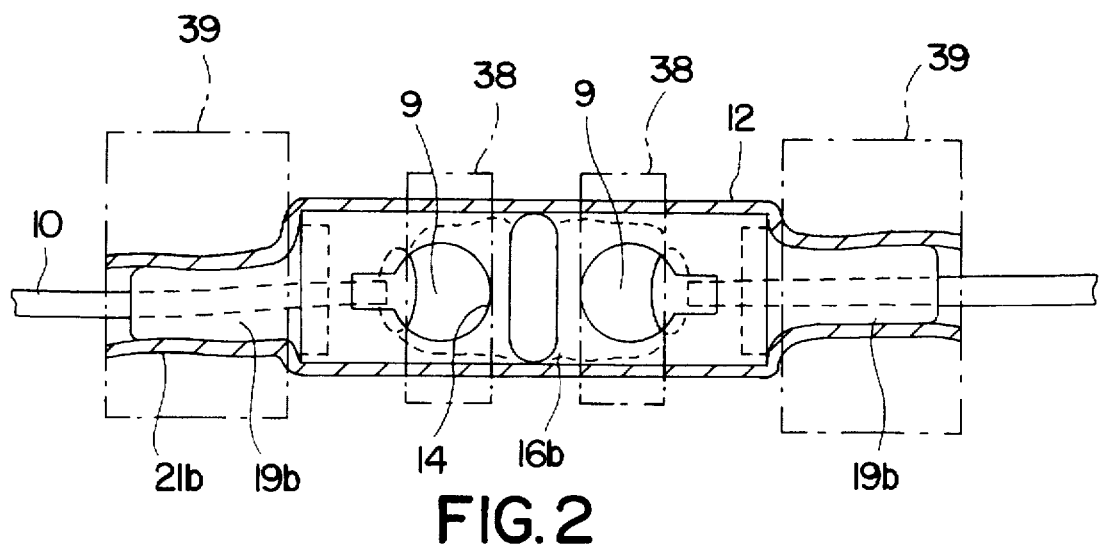
FIG. 2 is a diagram showing an operation of the embodiment.

The color image pickup 33 picks up an image of the connector 11 in the above state (first, second or third image pickup step). At this stage, the color image of the connector 11 used to extract the component color image or image color component to be described later and a binary image of the connector 11 are obtained and stored, for example, in a memory provided in the image extracting device 34. The contour of the connector 11 is obtained based on the obtained binary image, and soldering checking windows 38 (first area) and hot melt checking windows 39 (second and third areas) as shown in FIG. 2 are set. A pair of soldering checking windows 38 are set in areas at least partly including the check holes 14 of the metal tube 12 as indicated by phantom line in FIG. 2, whereas a pair of hot melt checking windows 39 are set in areas at least partly including molten hot melts 19b.

Next, whether or not the cores are satisfactorily soldered to the inner wall of the metal tube 12 is determined.

Specifically, component images of the color of the cores 9 are extracted from the color images within the soldering checking windows 38 by the image extracting device 34. If the cores 9 are made of copper, red component images are extracted as component images of the color of the cores 9. Accordingly, if the cores 9 are not satisfactorily soldered due to insufficient heating and therefore are left exposed from the solder 16b, images of the exposed portions of the cores 9 are extracted as component images of the color of the cores 9 (first image extraction step).

A non-soldered area of the cores 9 is calculated by the image processor 35 based on the extracted component images of the color of the cores 9 (non-soldered area calculation step).

Thereafter, the discriminator 36 compares the non-soldered area with a predetermined first threshold value. The discriminator 36 determines that the soldering is not satisfactory if the non-soldered area is larger than or equal the first threshold value, while determining that the soldering is satisfactory if the non-soldered area is smaller than the first threshold value (first determination step).

The determination result is displayed on an unillustrated external monitor.

Since the soldered state of the cores 9 is checked in this manner, the checking of a uniform quality can be always performed and a defective soldering of the cores 9 can be detected with an enhanced accuracy.

Whether or not the hot melts 19a were satisfactorily softened is determined as follows. Color images of the hot melts 19a after heating within the hot melt checking windows 39 are obtained, and the image extracting device 34 extracts component images of the color of the hot melts 19a before heating from the obtained color images. For example, if the hot melts 19a are blue before heating and become transparent after heating, blue component images are extracted. If the hot melts 19a were not satisfactorily softened due to insufficient heating, a non-softened area of the hot melts 19a is extracted as blue component images.

Then, the image processor 35 calculates the non-softened area of the hot melts 19a based on the extracted blue component images of the hot melts 19a (non-softened area calculation step).

Thereafter, the discriminator 36 compares the non-softened area with a predetermined second threshold value. The discriminator 36 determines that the hot melts 19a were not satisfactorily softened if the non-softened area is larger than or equal to the second threshold value, while determining that they were satisfactorily softened if the non-soldered area is smaller than the first threshold value (second determination step).

The discrimination result is displayed on the unillustrated external monitor.

Since the softened state of the hot melts 19a is checked in this manner, the checking of a uniform quality can be always performed and a defective softening of the hot melts 19a can be detected with an enhanced accuracy.

A carbonized state of the connector 11 may be checked in a process similar to the above. Specifically, upon carbonization, the color of the connector 11 changes to black. Accordingly, the image extracting device 34 extracts black component images from the color images within the windows 39 (third image extraction step) and the image processor 35 calculates a carbonized area based on the black component images (carbonized area calculation step). The discriminator 36 compares the carbonized area with a predetermined third threshold value, and determines that the connector 11 is carbonized if the carbonized area is larger than or equal to the third predetermined value while determining that the connector 11 is not carbonized if the carbonized area is smaller than the third predetermined value (third determination step).

According to the above method, the carbonized state of the connector 11 can be checked with a uniform quality and the carbonized connector 11 can be detected with an enhanced accuracy.

Figure 6:
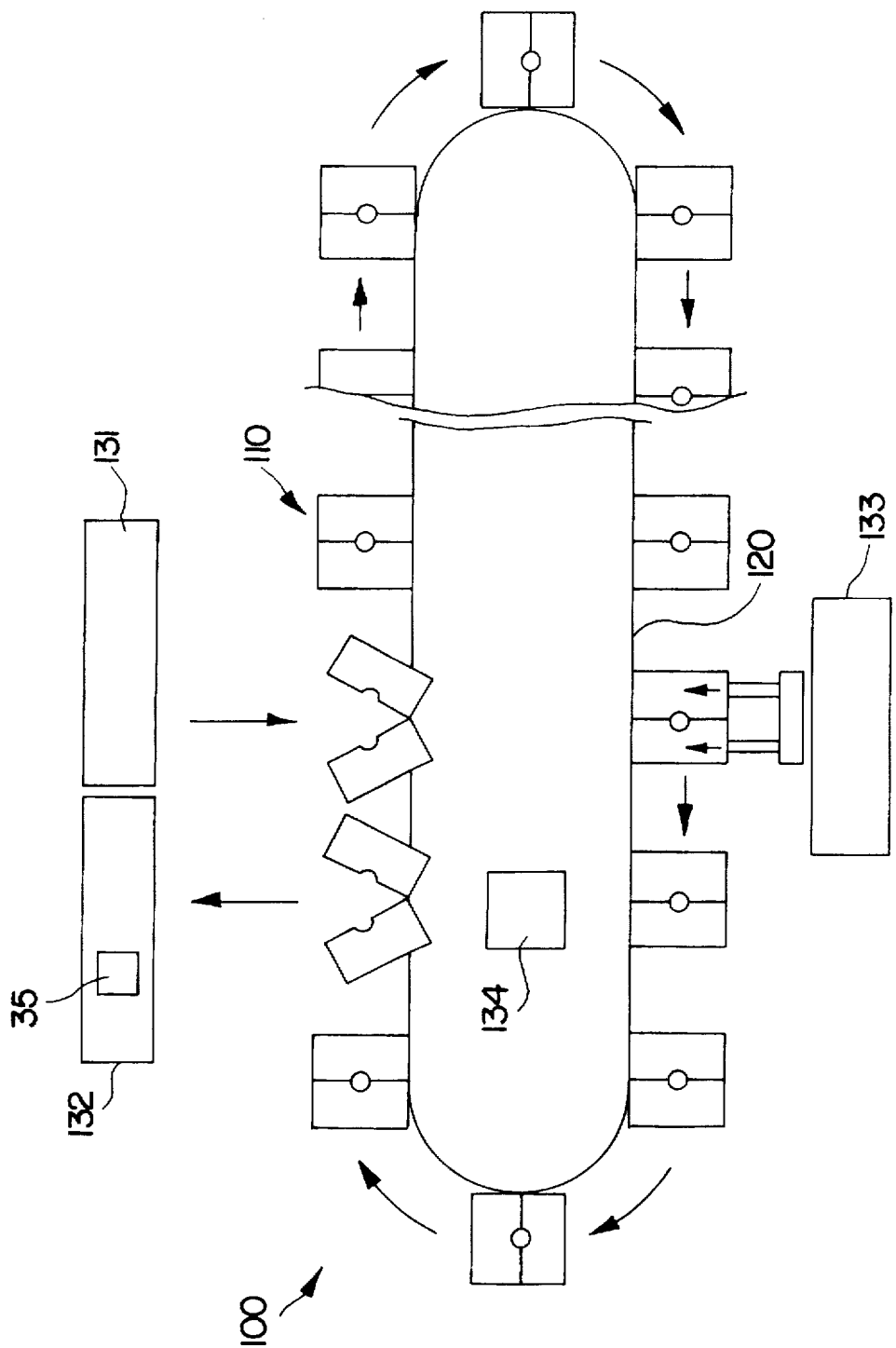
FIG. 6 is a schematic diagram of a heating apparatus for use with the connection checking apparatus of FIG. 1.

Further, a heater for heating the connector 11 may be controlled based on the thus obtained determination results. Specifically, the data concerning the respective determination results are transferred to a heating apparatus 100 as illustrated in FIG. 6. The heating apparatus 100 includes a plurality of closable heating units 110 arranged at specified intervals, a conveyor 120 for conveying the heating units 110 along a loop-shaped conveyance path including a loading or setting station 131 an unloading station 132, a cooling station 133 and a controller 134 for controlling the heating of the units 110. The checking apparatus described above and illustrated in detail in FIG. 1 is disposed at the unloading station 132 in FIG. 6. If the soldering by the solder 16b is determined to be unsatisfactory in the first determination step, it means insufficient heating. Accordingly, the heater controller 134 increases a heating temperature of the heater or prolongs a heating time thereof (first automatic heating control step). If the softening of the hot melts 19a is determined to have been unsatisfactory in the second determination step, it also means insufficient heating. Accordingly, in this case as well, the heater controller 134 increases the heating temperature of the heater or prolongs the heating time thereof (second automatic heating control step). Further, if the connector 11 is determined to be carbonized in the third determination step, it means excessive heating. Accordingly, the heater controller 134 decreases the heating temperature of the heater or shortens the heating time thereof (third automatic heating control step).

A next connector heating operation is suitably adjusted by automatically controlling the heating temperature and the heating time of the heater based on the respective determination results by means of the heater controller 134. This effectively prevents a defective connection of wires.

According to the wire connection checking method as described above, the connection of the wires can be checked with a uniform quality and a defective connection can be detected with an enhanced accuracy.

What is claimed is:

1. A method for checking a connection of electric wires (10), comprising:

a first image pickup step of picking up a color image of a first region (38) of a connection region (38; 39), by means of color image pickup means (33), the first region including at least part of an area of soldering of the electric wires (10), and a second image pickup step of picking up a color image of a second region (39) of the connection region (38; 39) by means of the color image pickup means (33), the second region (39) including at least part of an area of hot melt (19a, 21b) of the connector (11), an image extraction step of extracting at least one predeterminable image color component from each of the color images, a defect area calculation step of calculating an area of defect from each of the extracted image color components, and a determination step of determining whether the connection and hot melt area are satisfactory based on the defect area calculation step.

2. A method according to claim 1, wherein the determining in the determination step is performed based on the defect areas determined in the defect area calculation step.

3. A method according to claim 1, wherein the image extraction step comprises extracting a predeterminable first image color component of a color of the wires (10) from the color image picked up in the first image pick up step.

4. A method according to claim 3, wherein the wires (10) have conductive cores (9), the connection comprising soldering the cores (9) into electrical connection, and wherein the defect area calculation step comprises a non-soldered area calculation step of calculating a non-soldered area of the defect area based on the color of the cores (9) of the wires (10).

5. A method according to claim 4, wherein the determination step comprises determining that the cores (9) of the wires (10) are satisfactorily soldered when the calculated non-soldered area is smaller than a first threshold value, while determining that the cores (9) of the wires (10) are not satisfactorily soldered when the calculated non-soldered area is larger than or equal to the first threshold value.

6. A method according to claim 1, wherein the image extraction step comprises extracting a predeterminable image color component of a color of the hot melt means (19a, 21b) of the connector (11) before heating from the color image picked up in the second image pick up step.

7. A method according to claim 6, wherein the defect area calculation step comprises a non-softened area calculation step of calculating a non-softened area of the hot melt means (19a, 21b) of the defect area from the extracted image color component of the color of the hot melt means (19a, 21b).

8. A method according to claim 7, wherein the determination step comprises determining that the hot melt means (19a, 21b) was satisfactorily softened when the calculated non-softened area is smaller than a threshold value while determining that the hot melt means (19a, 21b) was not satisfactorily softened when the calculated non-softened area is larger than or equal to the threshold value.

9. A method according to claim 1, wherein the image pickup step comprises a third image pickup step of picking up a color image of a predetermined third region of the connection region by means of the color image pickup means (33).

10. A method according to claim 9, wherein the image extraction step further comprises extracting a black image component from the color image picked up in the third image pick up step.

11. A method according to claim 10, wherein the defect area calculation step further comprises a carbonized area calculation step of calculating a carbonized area of the connection from the extracted black image component.

12. A method according to claim 11, wherein the determination step further comprises determining that the connection is not carbonized when the calculated carbonized area is smaller than a threshold value while determining that the connection is carbonized and thus unsatisfactory, when the calculated carbonized area is larger than or equal to the threshold value.

13. A method according to claim 12, further comprising an automatic heating control step of automatically decreasing a heating temperature of a heating means or shortening a heating time of the heating means when the connection is determined to be carbonized in the determination step.

14. A method according to claim 13 further comprising an additional automatic heating control step of automatically increasing at least one of a heating temperature or a heating time of the heating means when at least one of the connection and a softening of the hot melt means (19a, 21b) is determined to be unsatisfactory in the determination step.

* * * * *